Figure 1:
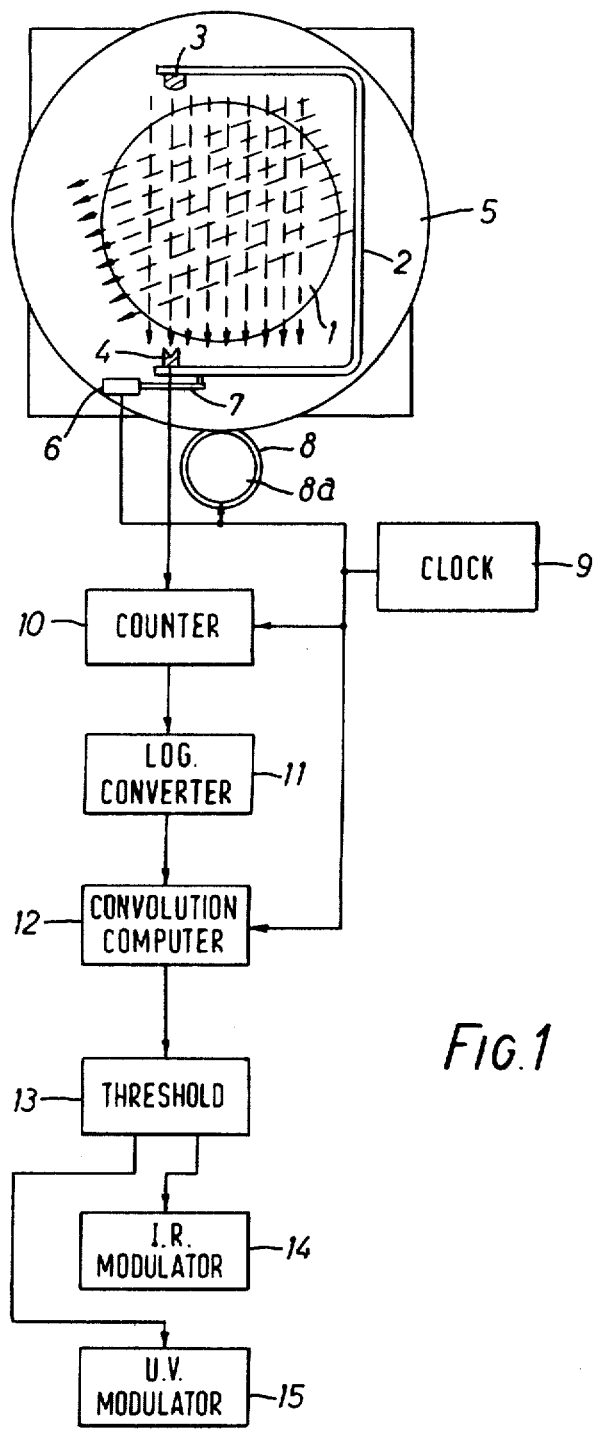

United States Patent [19]
Hounsfield

[11] 3,932,757
[45] Jan. 13, 1976

[54] APPARATUS FOR PRODUCING A VISUAL REPRESENTATION OF A RADIOGRAPHIC SCAN

[75] Inventor: Godfrey Newbold Hounsfield, Newark, England

[73] Assignee: EMI Limited, Hayes, England

[22] Filed: Apr. 18, 1974

[21] Appl. No.: 462,103

[30] Foreign Application Priority Data
May 5, 1973 United Kingdom............... 21524/73

[52] U.S. Cl. ................ 250/365; 250/329; 250/369
[51] Int. Cl.² ........................................... G01T 1/20
[58] Field of Search .......... 250/362, 366, 369, 329, 250/330, 336

[56] References Cited
UNITED STATES PATENTS
2,996,617 8/1961 Heckscher .......................... 250/329

3,549,887 12/1970 Hansen .............................. 250/369

Primary Examiner—Davis L. Willis
Attorney, Agent, or Firm—Fleit & Jacobson

[57] ABSTRACT

Apparatus is disclosed for providing a visual representation of the absorption or transmission coefficients of the elements of a two dimensional matrix of elements notionally defined in a cross-sectional plane through a body. The representation is in the form of an analogue display comprising superimposed lines of information scanned on the surface of a suitable screen, the brightness of each line being indicative of the absorption suffered by penetrating radiation on traversing a respective path through said plane of the body. The orientation of each scanned line depends on the orientation of the respective path with respect to the body.

7 Claims, 4 Drawing Figures

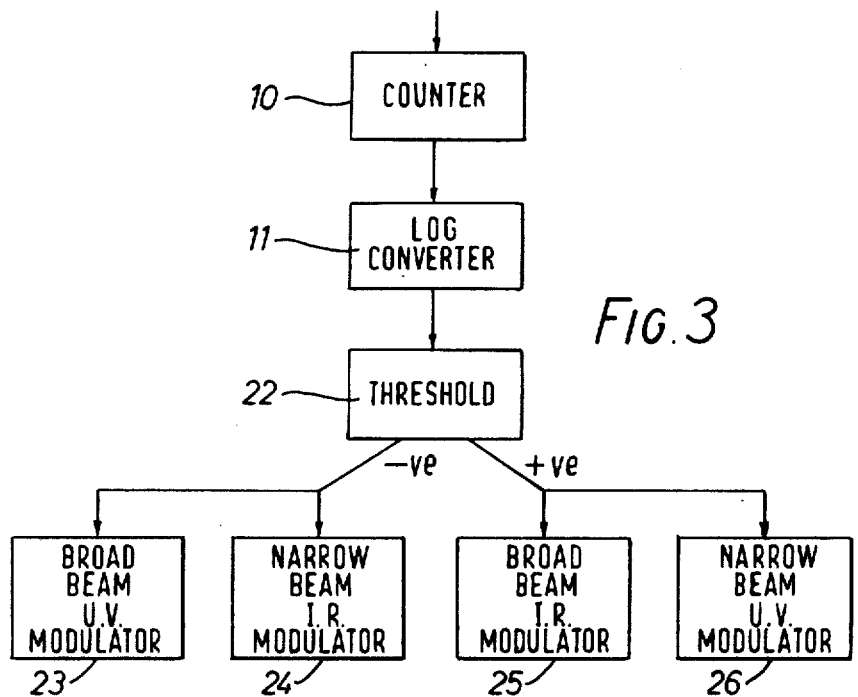
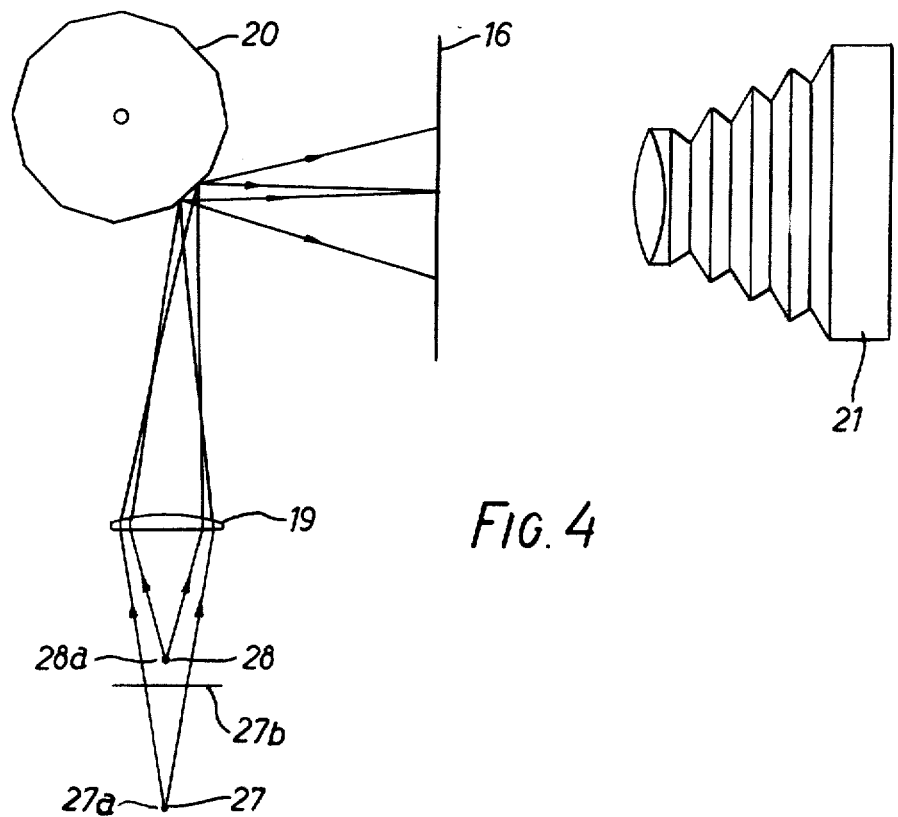

APPARATUS FOR PRODUCING A VISUAL REPRESENTATION OF A RADIOGRAPHIC SCAN

This invention relates to apparatus for examining a body by means of penetrating radiation such as X- or γ- radiation.

It has been proposed to form a radiograph of a region of a body by measuring the absorption of each of a plurality of rays of said radiation passed through the region in a precisely determined manner such that at least some of the rays intersect. Our United States Pat. No. 3,778,614 describes and claims apparatus for (and a method of) forming such radiograph, by computing the absorption (or transmission) coefficients of different ones of a plurality of elements in a matrix of elements notionally delineated in the region, from measured absorptions of the rays by a calculation including a series of successive approximations.

In this specification, the measured absorption of a ray will be referred to as an edge value, and the absorption (or transmission) coefficient assigned to a particular element in said matrix will be referred to as a mesh value.

The main object of the present invention is to provide apparatus for examining a body by means of radiation such as X- or γ- radiation including means for deriving, from a planar region of the body, electrical signals indicative of the absorption suffered by the radiation on traversing a plurality of sets of linear paths through the body, and having improved means for transforming said electrical signals into a visible display of the absorption coefficients of the elements of said planar region.

Figure 2:
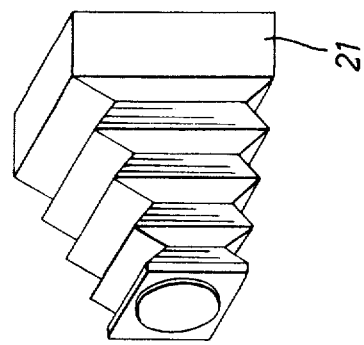
Figure 2:
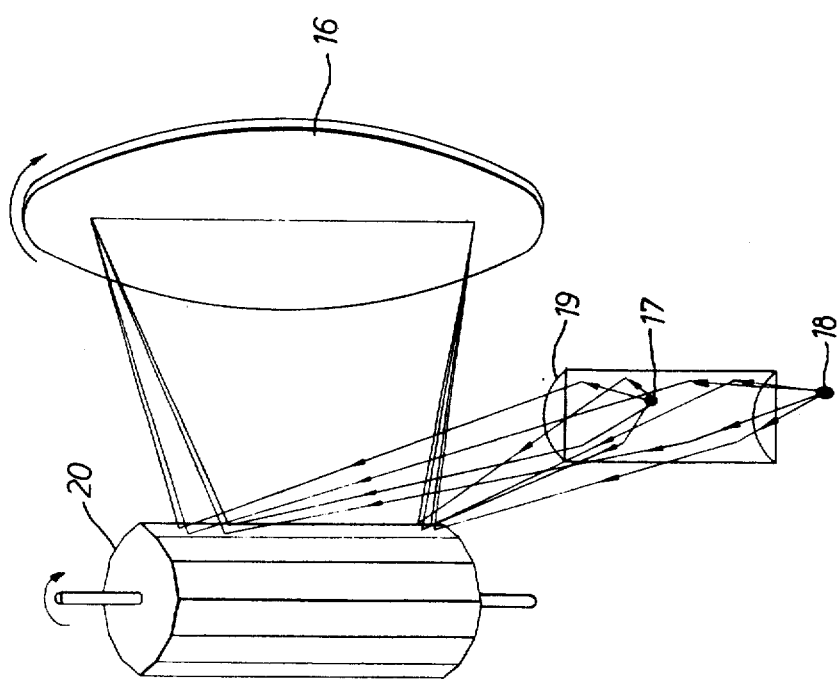

In order that the invention may be fully understood and readily carried into effect, one embodiment thereof will now be described with reference to the accompanying drawings of which:

FIG. 1 shows part of one example of apparatus in accordance with the invention for examining a body, FIG. 2 shows a display arrangement for use with the apparatus shown in FIG. 1, FIG. 3 shows an alternative arrangement suitable for use as part of the apparatus shown in FIG. 1, and FIG. 4 shows apparatus for displaying signals derived by the apparatus shown in FIG. 3.

FIG. 1 shows apparatus for passing sets of parallel rays of radiation through a region, defined by an aperture 1, in a plurality of different directions. Two such sets of ray paths are shown as hatched lines. A frame member 2 locates a source 3 of X-radiation and a radiation detector 4 on opposite sides of the aperture. The source 3, which conveniently comprises a Coolidge tube, is arranged to pass a collimated ray to detector 4, which detector, in this example of the invention, comprises a sodium iodide scintillation crystal with an associated photomultiplier tube. The frame 2 is arranged to perform a reciprocating motion relative to a discoidal backplate member 5, the frame 2 being driven by a reciprocating motor 6 and an associated connecting rod 7. In the position shown, the frame performs a right-left-right motion. The backplate 5 is capable of rotating in the plane of reciprocation of frame 2, being driven by a gear wheel 8a, which itself is driven by a motor 8. Motor 8 operates in a stepwise manner in response to electrical pulses from clock 9, and motor 6 is controlled by the same pulses. The photons detected by detector 4 are counted in a counter 10, the contents of which are read out in response to pulses from the clock 9, and are applied to a logarithmic converter which produces analogue signals of amplitude indicative of the logarithms of numbers read out of the counter 10.

In operation, the frame 2 is arranged to move in a regular manner across the aperture such that tube 3 produces a sweep of parallel rays through the region. The detector 4 detects, in turn the photon intensity of each ray after traversing the region, the pulse output of the photomultiplier for each ray being counted in counter 10 during the movement of frame 2. When the sweep is completed, motor 8 rotates the backplate 5 through an angular step, and a similar sweep is performed at an angle to the first sweep, but with the direction of motion of the frame reversed. A series of such sweeps is performed at a plurality of different angles.

It will be realised that the output of the logarithmic converter 11 comprises a series of signals indicative of edge values. Each of the signals has an amplitude indicative of the overall amount of the radiation absorbed by the notional elements through which the corresponding ray traverses. Sets of said edge value signals, each set corresponding to one of the sweeps of rays, are applied sequentially to a convolution computer 12. In this example of the invention, the convolution computer computes a set of signals representative of edge values from each of the aforementioned sets of edge values, which comprise convoluted edge values in accordance with the proposal elucidated in copending U.S. Pat. application Ser. No. 462,104. However, the computer 12 may alternatively be programmed in accordance with any other suitable transformation process.

As explained with reference to FIG. 8b, c and d of our U.S. Pat. No. 3,778,614, the range of absorption coefficients to be displayed depends on the overall absorption of radiation by the body and it is thus convenient to display the absorption coefficients as positive and negative values relative to a threshold or datum level. To achieve this end, output signals from the computer 12, indicative of the convoluted edge values, are applied to a threshold circuit 13 which processes the signals to become positive or negative signals relative to the threshold level. The threshold level may be varied depending upon the required range of absorption to be investigated. The positive and negative signals are arranged to modulate sources of ultra-violet (U.V.) and infrared (I.R.) energy respectively by means of respective modulators 14 and 15. These modulators may comprise, for example, Kerr Cell arrangements or means for controlling the supply voltages to the said sources of energy. The modulated energy is displayed as will now be described with reference to FIG. 2.

The display apparatus comprises a rotatable screen 16 having a phosphor coating which has the property of accumulating an afterglow when irradiated with U.V. radiation, the afterglow being reduced when the screen is irradiated with I.R. radiation. The phosphor layer may comprise zinc sulphide. Coincident lines of U.V. and I.R. radiation from the modulated sources shown as 17 and 18 are focussed on the screen 16 by means of a cylindrical lens 19, and are arranged to be scanned over the screen by means of a rotatable mirror drum 20. The rotation of the mirror drum is arranged to display a series of parallel lines on the screen 16 which have a relative spacing corresponding to rays of X-radiation in one of said sweeps through the body, and the screen 16 is rotated such that several series of parallel lines are displayed at different angles corresponding to different ones of said sweeps. The rotation of the screen 16 is effected by a drive from motor 8 and the mirror drum 20 may be driven by a motor controlled by the clock pulses from clock 9.

In operation, the screen 16 is exposed to an U.V. source such that a uniform afterglow is established in the phosphor layer. This may be achieved by scanning the line of U.V. radiation from source 17, when unmodulated, by means of mirror drum 20. The above-mentioned sets of lines are then displayed on the screen, the uniform afterglow of the screen being enhanced or degraded for each line in dependence upon the modulation signals applied to either of the modulators 14 or 15. Thus each line has a relative disposition corresponding to a particular one of said rays of X-radiation and has a uniform intensity afterglow indicative of the convoluted edge value attributed to the ray.

The afterglow of intersecting lines tend to sum at the intersections thereof so as to provide a spatial sum of the convoluted edge values in accordance with the previously mentioned Patent Application. The afterglow is liberated as visible light by directing a beam of I.R. radiation to the screen, for example by scanning the source 18, when unmodulated across the screen by means of mirror drum 20. The visible light released from the screen is recorded by an adjacent camera 21 to provide a photographic record indicative of a map of the variations in absorption coefficient in a section of the body defined by the locus of the rays of X-radiation.

Instead of computing the convoluted edge values by means of computer 12, the convolution may be performed in analogue manner with further beams of radiation arranged to be incident on screen 16. Referring now to FIG. 3, signals from an arrangement for scanning the body are processed by a counter 10 and log converter 11 in the manner described with reference to FIG. 1, and are subsequently applied to a threshold circuit 22 substantially similar to threshold 13. Positive and negative signals from the threshold 22 indicative of edge values are each applied to a respective pair of modulators, each pair including a modulator for a source of I.R. radiation and U.V. radiation, i.e., modulators 23, 24, 25 and 26. FIG. 4 shows a schematic arrangement for displaying such modulated radiation. References 27 and 28 show respectively sources of I.R. and U.V. radiation (modulated by modulators 25 and 26 respectively) which are focussed by means of a cylindrical lens 19 and via a mirror drum 20 to a rotatable screen 16 as described before. The I.R. source 27 is placed further from the lens 19 than the U.V. source 28 such that the former forms a broad line on the screen, while the latter forms a narrow line thereon as described with reference to FIG. 2. The intensity distribution across the broad beam is modified by a variable density filler 27b located as shown close to the source 28, to provide an intensity distribution across the plane of the screen 12 indicative of a convolution distribution, for example of the kind disclosed in aforementioned copending Patent Application. Considering first only positive edge values relative to the threshold level, the U.V. source 28 is modulated, by modulator 26, to augment by varying amounts a preset uniform afterglow on screen 16 in series of parallel lines, in a similar manner to that described before. The broad beam from I.R. source 27, however, degrades the afterglow for parallel lines adjacent and including that described by source 28 at any instant, so as to provide a correction to those lines in accordance with the proposals of the aforementioned Patent Application. A similar set of sources comprising a U.V. source 27a and an I.R. source 28a are placed beneath sources 27 and 28 and are modulated by negative signals from the threshold 22 thereby imparting an afterglow indicative of negative edge values relative to the threshold on the screen. Thus when all the edge values in a set of edge values have been displayed as a series of parallel lines, together with their corrections, a spatial afterglow distribution is recorded on the screen indicative of corresponding convoluted edge values. After several such series of parallel lines have been recorded on the screen 16, a map of the absorption ceefficients described by the retained afterglow is recorded by camera 21 in the manner described with reference to FIG. 2.

The signals indicative of edge values derived from the body need not necessarily be obtained by means of the scanning arrangement shown in FIG. 1, and may be derived from any other suitable apparatus. The display apparatus described with reference to FIG. 2 need not necessarily display convoluted edge values. To provide a crude display, the signals indicative of edge values with no other transformation than that produced by the log converter 11 may be processed directly in a threshold circuit such as 13 and then applied to the modulators 14 and 15.

What I claim is:

1. Apparatus for examining a body by means of radiation such as X- or γ- radiation including means for deriving, from a planar region of the body, electrical signals indicative of the absorption suffered by the radiation on traversing a plurality of sets of linear paths through the body, means for transforming said electrical signals in accordance with a convoluting function, visual display means including a screen device for displaying, in respect of each of said paths, a visible line of brightness determined by the transformed electrical signal derived from that path, each displayed line being oriented upon said screen device at an angle corresponding to the angle of the corresponding linear path through said region of the body.

2. Apparatus for examining a body by means of radiation such as X- or γ- radiation including means for deriving, from a planar region of the body, electrical signals indicative of the absorption suffered by the radiation on traversing a plurality of sets of linear paths through the body, means for transforming said electrical signals in accordance with a desired function, a screen device, sources of energy of two different wavelengths, means for focussing the energy of both wavelengths as coincident lines on said screen device, the screen device including material which stores energy when bombarded by energy of one of said wavelengths and releases energy when bombarded by energy of the other, means for comparing each transformed electrical signal with a threshold level, means for utilising signals in excess of said threshold level to control the strength of the energy of said one wavelength as incident on the screen device and for utilising the signals which do not exceed said threshold level to control the strength of the energy of said other wavelength as incident on the screen device, and means for scanning said coincident lines relative to said screen device to cause said lines to represent successively said sets of linear paths.

3. Apparatus according to claim 2 wherein said one wavelength lies in the ultra-violet band of the electromagnetic spectrum, and said other wavelength lies in the infra-red band of said spectrum.

4. Apparatus according to claim 3 wherein the material included in said screen device is zinc sulphide.

5. Apparatus according to claim 4 including means operative subsequently to the bombardment of the screen device by the energy from said sources to cause energy of said other wavelength and of uniform strength to be incident on the screen to liberate residual energy stored thereon as visible light.

6. Apparatus according to claim 2 including further sources of energy of said two different wavelengths so positioned that said focussing means causes energy from said source to impinge on said screen device as broad lines, variable density filter means to provide an intensity distribution of energy across said broad lines, and means for utilising the signals which do not exceed said threshold to control the strength of the energy from said further sources of said one wavelength as incident on said screen device and for utilising the signals in excess of said threshold level to control the strength of the energy from said further sources of said other wavelength as incident on said screen device, said scanning means being operative to scan said broad lines together with said first mentioned lines.

7. Apparatus according to claim 6 wherein said scanning means includes a rotatable mirror drum having a plurality of facets, the energy being incident thereon through a cylindrical lens.

* * * * *